United States Patent
Fernandez

Patent Number: 5,897,497
Date of Patent: Apr. 27, 1999

[54] GUIDING CATHETER INTRODUCER ASSEMBLY

[75] Inventor: Juan Carlos Fernandez, Miami, Fla.

[73] Assignee: Cordis Corporation, Miami Lakes, Fla.

[21] Appl. No.: 08/508,098

[22] Filed: Jul. 27, 1995

[51] Int. Cl.⁶ .................................................. A61B 6/00
[52] U.S. Cl. ............................................ 600/435; 609/280
[58] Field of Search ................................ 604/280, 281, 604/282, 283, 164, 165.7, 158; 128/658; 600/433–434, 435

[56] References Cited

U.S. PATENT DOCUMENTS

| | | | |
|---|---|---|---|
| 4,650,472 | 3/1987 | Bates ....................................... | 128/658 |
| 4,665,604 | 5/1987 | Dubowik . | |
| 5,045,072 | 9/1991 | Castillo . | |
| 5,066,285 | 11/1991 | Hillstead . | |
| 5,171,232 | 12/1992 | Castillo . | |
| 5,300,032 | 4/1994 | Hibbs et al. . | |
| 5,324,262 | 6/1994 | Fischell et al. . | |
| 5,389,090 | 2/1995 | Fischell et al. . | |
| 5,397,310 | 3/1995 | Chu et al. ................................ | 604/158 |
| 5,413,561 | 5/1995 | Fischell et al. .......................... | 604/167 |
| 5,423,762 | 6/1995 | Hillstead . | |
| 5,514,236 | 5/1996 | Avellan et al. .......................... | 156/154 |
| 5,538,512 | 7/1996 | Zenzon et al. ........................... | 604/280 |
| 5,538,513 | 7/1996 | Okajima .................................. | 604/280 |
| 5,558,652 | 9/1996 | Henke ..................................... | 604/280 |

*Primary Examiner*—Max Hindenburg
*Assistant Examiner*—Pamela L. Wingood
*Attorney, Agent, or Firm*—Thomas Vigil; Henry Collins; Dean Garner

[57] ABSTRACT

A guiding catheter introducer assembly that includes a catheter introducer sheath, with a hemostasis valve, attached or molded to a reinforced guiding catheter tubular body into a single assembly. The reinforced guiding catheter tubular body is made of braided wire construction. The catheter introducer sheath assembly includes a side port at which point a multiport stop cock is attached or molded, to facilitate the insertion and withdrawal of fluids.

4 Claims, 3 Drawing Sheets

GUIDING CATHETER INTRODUCER ASSEMBLY

BACKGROUND OF THE INVENTION

1. Field of the Invention

The present invention relates to an intravascular guiding catheter assembly, for use in the insertion and removal of medical devices and/or fluids into a blood vessel of a patient.

2. Description of the related art including information disclosed under 37 CFR §§ 1.97–1.99.

Heretofore, various guiding and introducer catheters have been proposed. Several examples of analogous and non-analagous guiding and introducer catheter assemblies are disclosed in the following U.S. Pat. Nos:

| U.S. Pat. No. | Patentee |
| --- | --- |
| 5,066,285 | Hillstead |
| 5,300,032 | Hibbs et al. |
| 5,324,262 | Fischell et al. |
| 5,389,090 | Fischell et al. |

The Hillstead U.S. Pat. No. 5,066,285 discloses a catheter introducer with a sheath made of an expanded fibrous plastic, for gaining temporary entry into a patient's blood vessel with the use of a dilator. A catheter can subsequently be inserted into a patient's blood vessel after removal of the dilator through a hemostasis valve, located at the distal end of the catheter introducer sheath. The sheath features flexibility without kinking and high hoop strength.

The Hibbs et al. U.S. Pat. No. 5,300,032 discloses a catheter introducer with a rigid tubular body and a soft flexible tubular tip formed from a polymer material, such that the tip can navigate a greater curvature of a vessel wall without buckling. Attached to the proximal end of the tubular body is a valve and seal structure to prevent leakage during insertion and placement of the catheter.

The Fischell et al. U.S. Pat. No. 5,324,262 discloses an introducer sheath with an inflatable collar. The inflatable collar can be expanded to fit snugly against the edges of an opening in the blood vessel wall formed by the insertion of the introducer sheath to prevent blood leakage through the blood vessel wall. At a proximal section of the sheath is a proximal fitting containing a hemostasis valve.

The Fischell et al. U.S. Pat. No. 5,389,090 discloses a guiding catheter with an attached Touhy-Borst fitting. The guiding catheter uses a dilator and a guide wire to direct the catheter to its destination within a patient's artery without requiring an introducer sheath.

SUMMARY OF THE INVENTION

According to the present invention there is provided a guiding catheter introducer assembly that includes a catheter introducer sheath, with a hemostasis valve, attached or molded to a reinforced guiding catheter tube into a single assembly. The reinforced guiding catheter tube comprises a braided wire reinforced tubular body. The catheter introducer sheath further includes a side port at which point a stop cock can be attached or molded, again part of the single assembly, to facilitate the insertion and withdrawal of fluids.

By incorporating a braided wire reinforced guiding catheter tube into a catheter introducer assembly with a hemostasis valve attached thereto having a stopcock valve connected thereto into a single assembly, such assembly allows a physician to insert and place the guiding catheter directly into the body and start inserting medical devices through the hemostasis valve with minimal leakage of body fluids. Also liquids can be easily inserted into or withdrawn from the patient through the stopcock valve.

DESCRIPTION OF THE PREFERRED EMBODIMENT

Figure 1:
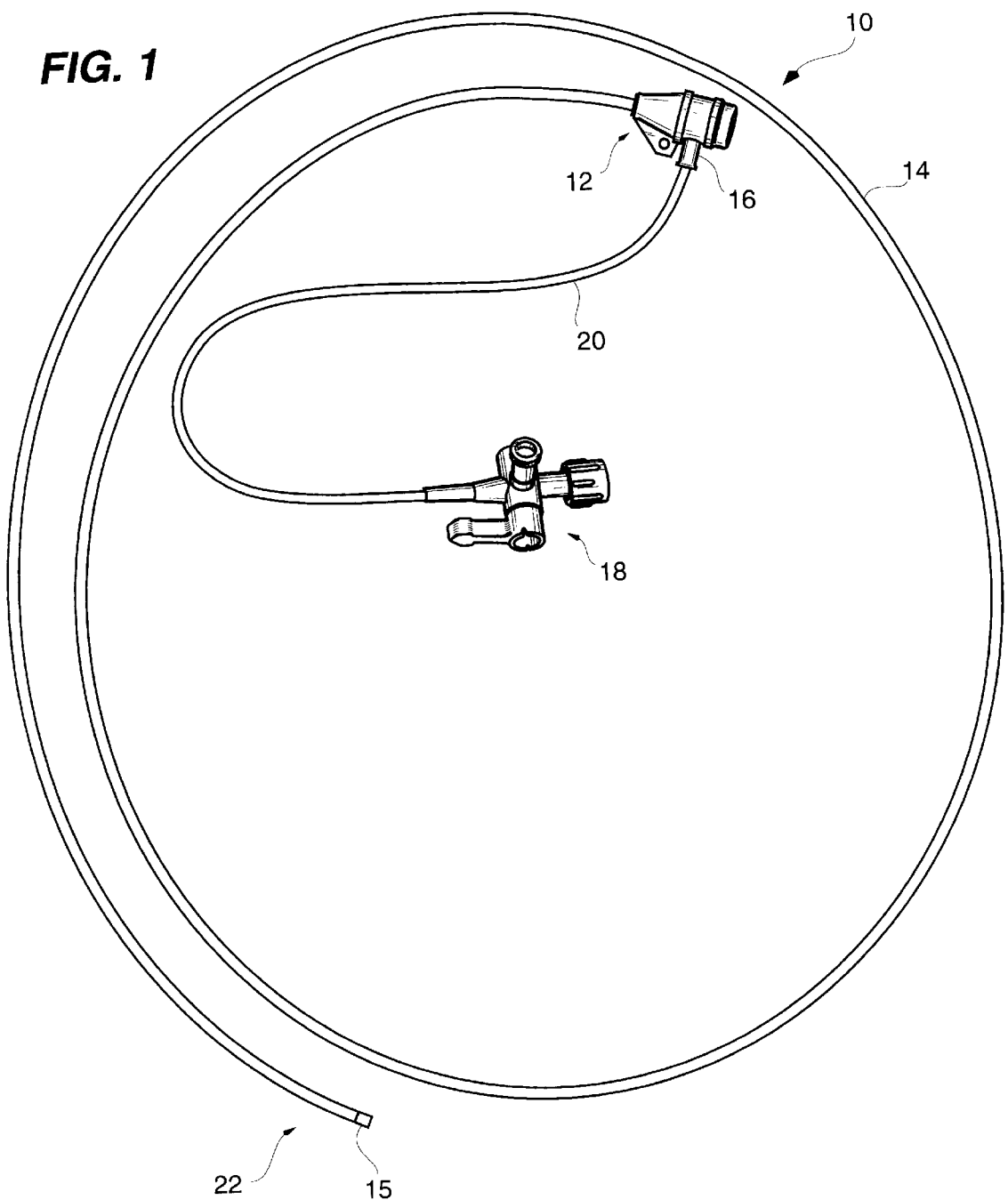
FIG. 1 is a perspective view of one embodiment of a guiding catheter introducer assembly constructed to the teachings of the present invention.

Referring now to the drawings in greater detail, there is illustrated in FIG. 1 a guiding catheter introducer assembly 10 constructed according to the teachings of the present invention. The guiding catheter introducer assembly 10 includes a catheter sheath introducer body 12 integrally attached to a guiding catheter tubular body 14.

Figure 4:
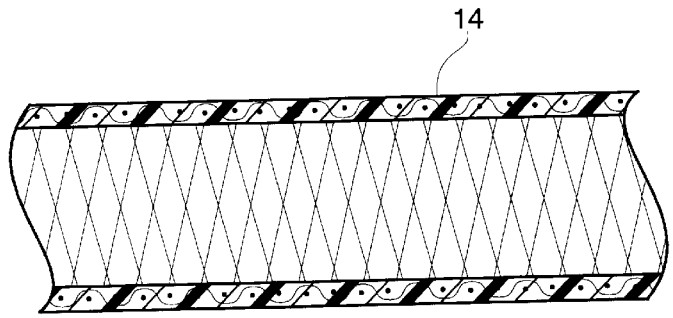
FIG. 4 is a cross section of the same reinforced guiding catheter tubular body shown in FIG. 3 and is taken along line 4—4 of FIG. 3.
Figure 3:
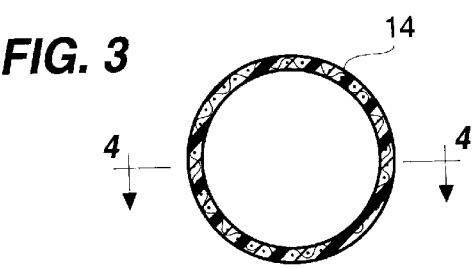
FIG. 3 is a cross section of one embodiment of a reinforced guiding catheter tubular body of the assembly and is taken along line 3—3 of FIG. 2.

The guiding catheter tubular body 14 (shown in FIGS. 3 and 4) has a stiff braid reinforced body similar to the catheter body described in Dubowik, U.S. Pat. No. 4,665,604 whose specification is incorporated herein by reference. A soft tip 15 is provided and is void of the stiff braid reinforcing.

A side port 16 extends laterally outward from the catheter sheath introducer body 12. Integrally attached to the side port 16 is a multiport stop cock 18 via a tubing 20. The interior of tubing 20 couples to side port 16 and allows fluids to transfer through the catheter introducer body 12 to the guiding catheter tubular body 14 from the side port 16 and the multiport stop cock 18.

At a distal end 22 of the guiding catheter tubular body 14, the tip 15 is coated with a radiopaque material such that it is visible on an x-ray machine when inserted into the patient. A more detailed description of such structure can be found in the Castillo et al. U.S. Pat. No. 5,045,072, and the Castillo et al. U.S. Pat. No. 5,171,232, whose specifications are incorporated herein by reference.

Figure 2:
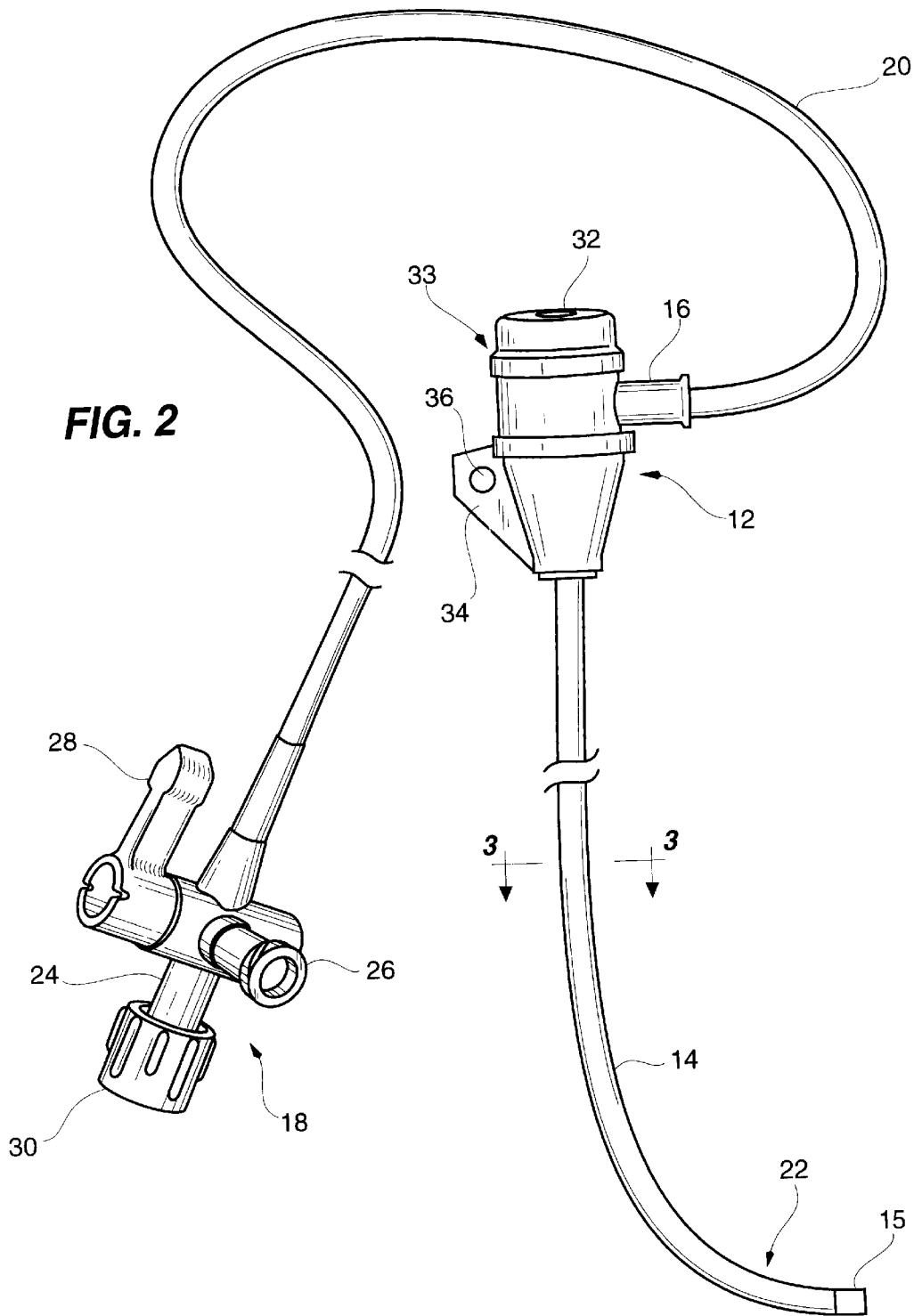
FIG. 2 is an exploded view of the same embodiment featured in FIG. 1 with the guiding catheter introducer assembly and a stop cock enlarged to show greater detail.

Referring now to FIG. 2, there is illustrated therein an enlarged view of the guiding catheter introducer assembly 10, highlighting in greater detail the catheter sheath introducer body 12 and the multiport stop cock 18.

The multiport stop cock 18 has two side ports 24 and 26 and a lever 28 for opening and closing a path between the opening at the end of the side ports 24 and 26 and the interior of the tubing 20. Additionally, shown attached to side port 24 is a Luer-lock™ connector 30. The multiport stop cock 18 allows fluids to be injected and withdrawn simultaneously as needed by the user.

The catheter sheath introducer body 12 has an opening 32 at the proximal end 33 of the catheter sheath introducer body 12. The opening 32 allows the user to insert or remove medical devices through the guiding catheter introducer assembly 10 into and out of the blood vessel and direct them to a desired location in the patient's body.

Molded to the side of the catheter sheath introducer body 12 is a rotatable annular flange 34 with an eyelet 36. The eyelet 36 can be used as a suture ring allowing the guiding catheter introducer assembly 10 to be stitched to the patient after the guiding catheter introducer assembly 10 has been inserted. This prevents movement of the guiding catheter introducer assembly 10 after it is secured in place.

Figure 5:
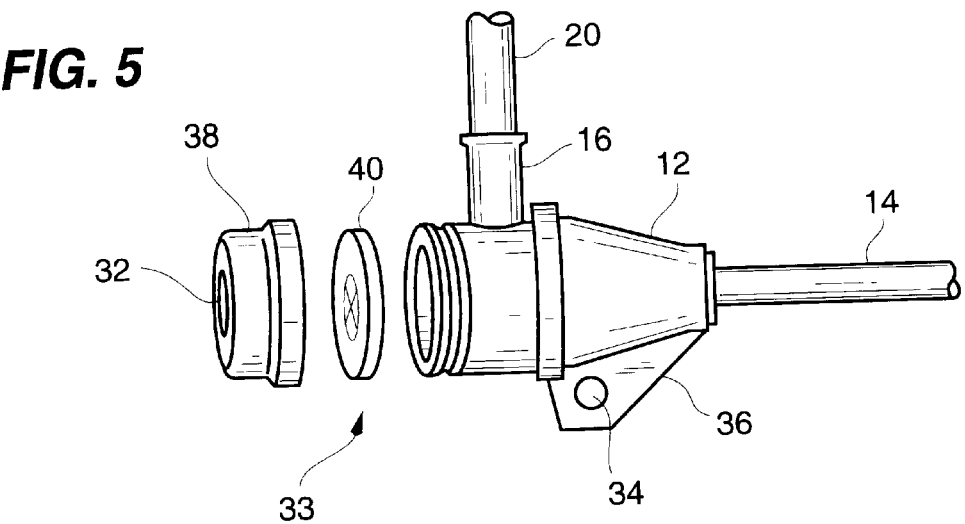
FIG. 5 is a partially exploded, perspective view of the guiding catheter sheath introducer assembly with an end cap portion removed and separated from a proximal end of the assembly to show a hemostasis valve of the assembly.

In FIG. 5 there is illustrated a catheter sheath introducer body 12 with an end cap portion 38 removed and separated from a proximal end 33 of the body 12. Within the catheter sheath introducer body 12, normally adjacent to the opening 32, is a hemostasis valve partition 40. The hemostasis valve partition 40 prevents the flow of fluids or gasses through the opening 32 when the user inserts or removes a medical device, such as an angioplasty balloon assembly into the patient through the guiding catheter introducer assembly 10.

Figure 6:
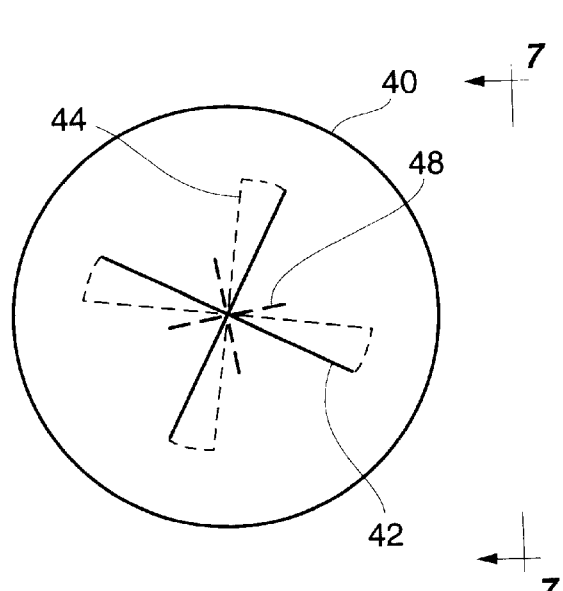
FIG. 6 is an enlarged plan view of the hemostasis valve partition.
Figure 7:
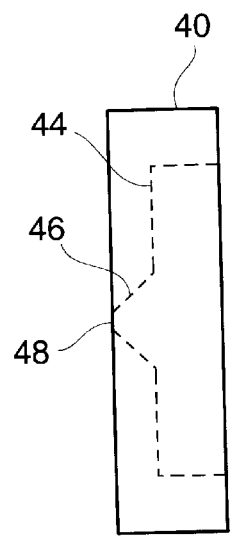
FIG. 7 is an elevational view of the same hemostasis valve partition shown in FIG. 6 and is taken along line 7—7 of FIG. 6.

The hemostasis valve partition 40 of the preferred embodiment is illustrated in FIG. 6 and FIG. 7. FIG. 6 shows a plan view of the hemostasis valve partition 40. FIG. 7 shows an elevational view of the hemostasis valve partition 40. Through the center of the valve partition 40 are cut slits in the form of a plurality of radii 42. As the slits extend into the valve partition 40 the radii 42 are rotated in a helical manner to a depth 44 between two-thirds to three-quarters of the overall thickness of valve partition 40. At which point the slits continue to extend at a reduced and diminishing diameter 46 until the slits extend the rest of the way through the end 48 of the valve partition 40.

The hemostasis valve partition 40 is preferably made of silicone rubber, but a variety of elastomers may also be used.

Of course, another type of hemostasis valve partition can be used in the assembly 10 and still achieve the benefits described and inherent in the present invention.

Because the guiding catheter introducer assembly 10 is meant to incorporate the functionality of both an introducer sheath and a guiding catheter the length of the guiding catheter tubular body 14 of the preferred embodiment of the guiding catheter introducer assembly 10 is minimally 80 centimeters in length, and preferably 100 to 110 centimeters, and has a central passageway which has a preferred diameter of French 9.

A guiding catheter tubular body 14 with length of approximately 100 will be able to reach most locations within the heart blood vessels to which a user should wish to access. A guiding catheter tubular body 14 with a central passageway of diameter French 9 will allow access for most devices, i.e. balloon catheters, which need to be inserted into the blood vessel including an additional guiding catheter.

Because the catheter sheath introducer body 12 is attached directly to the guiding catheter tubular body 14 as a single assembly, there is no need for assembly and disassembly of the unit for any reason, by the end user. Additionally only a single entry into the blood vessel wall is necessary, thereby reducing the trauma associated with entry into the blood vessel. The user merely inserts and places the guiding catheter introducer assembly 10 into position and starts inserting medical devices through the opening 32 and hemostasis valve partition 40 of the catheter sheath introducer body 12, as well as injection of agents or removal of fluids through the stop cock 18. When the user has completed the desired procedures, the user removes the entire assembly 10 and closes the blood vessel entry point.

From the foregoing description, it will be apparent that the guiding catheter introducer assembly 10 of the present invention has a number of advantages, some of which have been described above and others of which are inherent in the invention. Also it will be understood that modifications can be made to the guiding catheter introducer assembly described above without departing from the teachings of the invention.

I claim:

1. A guiding catheter and introducer assembly for insertion into a blood vessel of a patient comprising:

a catheter sheath introducer body;

a hemostasis valve attached to said catheter sheath introducer body and having a distal end, a proximal end and a central passageway therethrough opening onto both said proximal end and said distal end;

a guiding catheter tubular body which is flexible and resilient, which can be coiled and which has a distal end, a proximal end and a central passageway or lumen therethrough opening onto both said proximal end and said distal end, said guiding catheter tubular body including a self supporting wire braided reinforced tubular body including an elastomeric polvurethane resin, said proximal end of said guiding catheter tubular body being integrally attached to said distal end of said catheter sheath introducer body as a single unit such that said central passageway of said catheter sheath introducer body and said central passageway or lumen of said guiding catheter tubular body form a common continuous passageway which is large enough to receive a French 9 catheter;

said catheter sheath introducer body having a side port having a distal end, a proximal end and a central passageway therethrough opening onto both said proximal end and said distal end, said proximal end of said side port being in communication with said opening in said central passageway of said catheter sheath introducer body;

a stop cock assembly being integrally attached to the distal end of said side port;

said central passageway or lumen of said guiding catheter tubular body being coated or lined with a lubricous material to increase the lubricity thereof;

said guiding catheter tubular body having a radiopaque tip at said distal end of said guiding catheter tubular body; and, said guiding catheter tubular body having a length between approximately 80 centimeters and approximately 110 centimeters.

2. The guiding catheter and introducer assembly of claim 1, wherein said stop cock is a multiport stopcock.

3. The guiding catheter and introducer assembly of claim 1, wherein said catheter sheath introducer body further comprises a rotatable annular flange.

4. The guiding catheter and introducer assembly of claim 3, wherein said flange further comprises an eyelet for allowing the guiding catheter introducer assembly to be sewn to the patient.

* * * * *